United States Patent [19]

Oku et al.

[11] Patent Number: 5,708,172

[45] Date of Patent: Jan. 13, 1998

[54] INTERMEDIATES FOR SYNTHETIC USE AND PROCESSES FOR PRODUCING AMINOPIPERAZINE DERIVATIVES

[75] Inventors: Teruo Oku; Hiroshi Kayakiri, both of Tsukuba; Hirokazu Tanaka, Takarazuka, all of Japan

[73] Assignee: Fujisawa Pharmaceutical Co., Ltd., Osaka, Japan

[21] Appl. No.: 553,551

[22] PCT Filed: Jun. 8, 1994

[86] PCT No.: PCT/JP94/00933

§ 371 Date: Jan. 18, 1996

§ 102(e) Date: Jan. 18, 1996

[87] PCT Pub. No.: WO95/00502

PCT Pub. Date: Jan. 5, 1995

[30] Foreign Application Priority Data

Jun. 18, 1993 [JP] Japan .................. 5-172427

[51] Int. Cl.⁶ .............. C07D 295/28; C07D 295/32
[52] U.S. Cl. .............................. 544/382; 544/61
[58] Field of Search ................... 544/382; 560/51

[56] References Cited

U.S. PATENT DOCUMENTS

| | | | |
|---|---|---|---|
| 3,200,120 | 8/1965 | Lovell | 544/375 |
| 3,200,121 | 8/1965 | Lovell | 544/382 |
| 4,983,606 | 1/1991 | Casagrande et al. | 514/248 |
| 5,250,528 | 10/1993 | Oku et al. | |

FOREIGN PATENT DOCUMENTS

| | | |
|---|---|---|
| 3919175 | 9/1964 | Japan . |
| 151561 | 6/1989 | Japan . |
| 911979 | 2/1991 | WIPO . |

Primary Examiner—Mukund J. Shah
Assistant Examiner—Sabiha Qazi

Attorney, Agent, or Firm—Oblon, Spivak, McClelland, Maier & Neustadt, P.C.

[57] ABSTRACT

A novel industrial process excellent in yield and purity for preparing a compound of the formula:

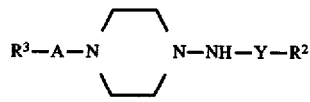

or a salt thereof, which comprises reacting a compound of the formula:

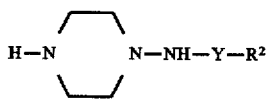

or a salt thereof with a compound of the formula:

$R^3$—A—OH or its reactive derivative or a salt thereof, wherein $R^2$ is cyclo(lower)alkyl, aryl or ar(lower)alkyl, each of which may be substituted with halogen, $R^3$ is lower alkyl, aryl, ar(lower)alkoxy or heterocyclic group, each of which may be substituted with halogen, A is

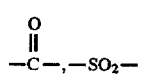

or lower alkylene and Y is

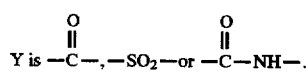

7 Claims, No Drawings

INTERMEDIATES FOR SYNTHETIC USE AND PROCESSES FOR PRODUCING AMINOPIPERAZINE DERIVATIVES

DESCRIPTION

1. Technical Field

The present invention relates to novel industrial processes excellent in yield and purity for preparing aminopiperazine derivatives and pharmaceutically acceptable salts thereof and to novel synthetic intermediates thereof and is useful in a pharmaceutical field.

2. Background Technology

The processes for preparing aminopiperazine derivatives of the present invention are described in an international patent application (international publication number WO91/01979) published based on the Patent Cooperation Treaty. By the said processes, however, isolation and purification of intermediate products are not necessarily easy owing to water-solubility thereof or the like and mass production of the aminopiperazine derivatives was difficult.

DISCLOSURE OF INVENTION

One object of the present invention is to provide novel processes for preparing the aminopiperazine derivatives and pharmaceutically acceptable salts thereof which possess the potentiation of the cholinergic activity and are useful for treating disorders in the central nervous system, especially for treating amnesia, dementia, senile dementia, and the like in human being.

Another object of the present invention is to provide novel synthetic intermediates useful for the processes for preparing the aforesaid aminopiperazine derivatives and pharmaceutically acceptable salts thereof.

The synthetic intermediates of the present invention are novel and can be represented by the following general formula:

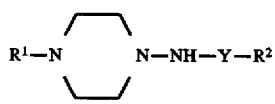

wherein $R^1$ is hydrogen or benzyloxycarbonyl, $R^2$ is cyclo(lower)alkyl, aryl or ar(lower)alkyl, each of which may be substituted with halogen, Y is $-\overset{O}{\underset{\|}{C}}-$, $-SO_2-$ or $-\overset{O}{\underset{\|}{C}}-NH-$.

According to the present invention, the aminopiperazine derivatives of the object compound (I) and pharmaceutically acceptable salts thereof can be prepared by the following processes.

Process 1

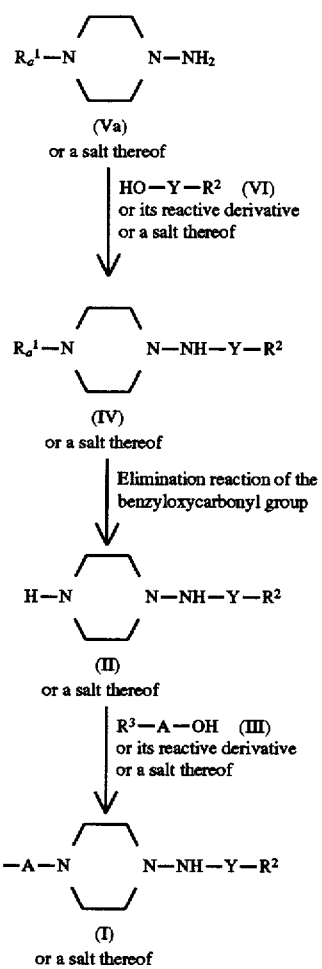

wherein $R^2$ and Y are each as defined above, $R^3$ is lower alkyl, aryl, ar(lower)alkoxy or heterocyclic group, each of which may be substituted with halogen, A is $-\overset{O}{\underset{\|}{C}}-$, $-SO_2-$ or lower alkylene and $R^1_a$ is benzyloxycarbonyl.

Process 2

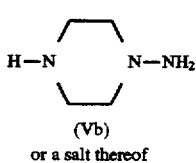
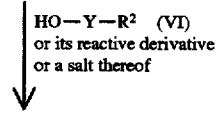

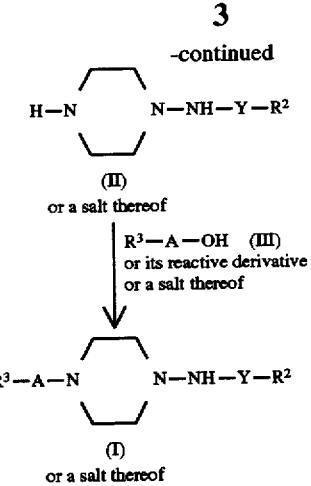

(II)

or a salt thereof $$R^3-A-OH \quad (III)$$
or its reactive derivative
or a salt thereof

[2]

↓

R³—A—N⟨  ⟩N—NH—Y—R²

(I)

or a salt thereof wherein $R^2$, $R^3$, A and Y are each as defined above.

In the above and subsequent descriptions of the present specification, suitable examples of the various definitions to be included within the scope of the invention are explained in detail as follows.

The term "lower" is intended to mean 1 to 6 carbon atom(s),unless otherwise indicated.

Suitable "lower alkyl" may include a straight or branched one such as methyl, ethyl, propyl, isopropyl, butyl, isobutyl, t-butyl, pentyl, hexyl, and the like, in which the preferable one is methyl.

Suitable "aryl" may include phenyl, naphthyl, tolyl, xylyl, mesityl, cumenyl, and the like, in which the preferable one is phenyl or naphthyl.

Suitable "ar(lower)alkoxy" may include benzyloxy, phenethyloxy, phenylpropoxy, benzhydryloxy, trityloxy, and the like.

Suitable "heterocyclic group" may include saturated or unsaturated monocyclic group containing at least one hetero-atom such as nitrogen, oxygen and sulfur atom.

Preferable "heterocyclic group" thus defined may be unsaturated 3 to 8-membered (more preferably 5 or 6-membered) heteromonocyclic group containing 1 to 4 nitrogen atom(s), for example, pyrrolyl, imidazolyl, pyrazolyl, pyridyl, pyridyl N-oxide, dihydropyridyl, tetrahydropyridyl, pyrimidyl, pyrazinyl, pyridazinyl, triazinyl, triazolyl, tetrazinyl, tetrazolyl, etc.;

unsaturated condensed heterocyclic group containing 1 to 5 nitrogen atom (s), for example, indolyl, isoindolyl, indolizinyl, benzimidazolyl, quinolyl, isoquinolyl, indazolyl, benzotriazolyl, etc.;

unsaturated 3 to 8-membered heteromonocyclic group containing 1 to 2 oxygen atom(s) and 1 to 3 nitrogen atom(s), for example, oxazolyl, isoxazolyl, oxadiazolyl, etc.;

saturated 3 to 8-membered heteromonocyclic group containing 1 to 2 oxygen atom(s) and 1 to 3 nitrogen atom(s), for example, morpholino, sydnonyl, etc.;

unsaturated condensed heterocyclic group containing 1 to 2 oxygen atom (s) and 1 to 3 nitrogen atom(s), for example, benzoxazolyl, benzoxadiazolyl, etc.;

unsaturated 3 to 8-membered heteromonocyclic group containing 1 to 2 sulfur atom(s) and 1 to 3 nitrogen atom(s), for example, thiazolyl, isothiazolyl, thiadiazolyl, etc.;

unsaturated 3 to 8-membered heteromonocyclic group containing 1 to 2 sulfur atom(s), for example, thienyl, etc.;

unsaturated condensed heterocyclic group containing 1 to 2 sulfur atom (s) and 1 to 3 nitrogen atom(s), for example, benzothiazolyl, benzothiadiazolyl, etc.;

unsaturated 3 to 8-membered heteromonocyclic group containing an oxygen atom, for example, furyl, etc.;

unsaturated condensed heterocyclic group containing 1 to 2 sulfur atom (s), for example, benzothienyl, etc.;

unsaturated condensed heterocyclic group containing 1 to 2 oxygen atom (s), for example, benzofuranyl, etc.,and the like.

Suitable "cyclo(lower)alkyl" may include cyclopropyl, cyclobutyl, cyclopentyl, cyclohexyl, and the like.

Suitable "ar(lower)alkyl" may include benzyl, phenethyl, phenylpropyl, benzhydryl, trityl, and the like.

Suitable "lower alkylene" may include methylene, ethylene, propylene, pentamethylene, hexamethylene, and the like.

Suitable "acid residue" may include halogen atom [e.g. fluoro, chloro, bromo and iodo], arenesulfonyloxy [e.g. bezenesulfonyloxy, tosyloxy, etc.], lower alkanesulfonyloxy [e.g. mesyloxy, ethanesulfonyloxy, etc.], and the like.

"Lower alkyl", "aryl", "ar(lower)alkoxy", "heterocyclic group", "cyclo(lower)alkyl" and "ar(lower)alkyl" described above may be substituted with halogen [e.g. fluoro, chloro, bromo and iodo].

Pharmaceutically acceptable salts of the object compound (I) are conventional non-toxic salts and may include an acid addition salt such as an inorganic acid addition salt [e.g. hydrochloride, hydrobromide, sulfate, phosphate, etc.], an organic acid addition salt [e.g. formate, acetate, trifluoroacetate, maleate, tartrate, methanesulfonate, benzenesulfonate, toluenesulfonate, etc.]; a salt with an amino acid [e.g. aspartic acid salt, glutamic acid salt, etc.]; and the like.

The processes for preparing the object compound (I) are explained in detail in the following.

Process 1

Subprocess [1]

The compound (IV) or a salt thereof can be prepared by reacting the compound (Va) or a salt thereof with the compound (VI) or its reactive derivative at the carboxy group or the sulfo group or a salt thereof.

Suitable salts of the compound (Va) can be reffered to the ones as exemplified for the compound (I).

Suitable reactive derivative at the carboxy group or the sulfo group of the compound (VI) may include an ester, an acid halide, an acid anhydride, and the like. Suitable examples of the reactive derivatives may be an acid halide [e.g. acid chloride, acid bromide, etc.]; a symmetrical acid anhydride; a mixed acid anhydride with an acid such as aliphatic carboxylic acid [e.g. acetic acid, pivalic acid, etc.], substituted phosphoric acid [e.g. dialkylphosphoric acid, diphenylphosphoric acid, etc.]; an ester such as substituted or unsubstituted lower alkyl ester [e.g. methyl ester, ethyl ester, propyl ester, hexyl ester, trichloromethyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphtyl ester, etc.], or an ester with N,N-dimethylhydroxylamine, N-hydroxysuccinimide, N-hydroxyphthalimide or 1-hydroxy-6-chloro-1H-benzotriazole. These reactive derivatives can optionally be selected from them according to the kind of the compound (VI) to be used.

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. A hydrophilic solvent may also be used in a mixture with water.

The reaction is preferably carried out in the presence of a conventional base such as triethylamine, pyridine, sodium hydroxide, or the like.

When the compound (VI) is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isopropyl chloroformate, etc.], 1-(p-chlorobenzenesulfonyloxy)-6-chloro-1H-benzotriazole, or the like.

The reaction temperature is not critical and the reaction is usually carried out under cooling to heating.

Subprocess [2]

The compound (II) or a salt thereof can be prepared by subjecting a compound (IV) or a salt thereof to elimination reaction of the benzyloxycarbonyl group.

Suitable salts of the compound (II) can be reffered to the ones as exemplified for the compound (I).

This elimination reaction is carried out in accordance with a conventional method such as hydrolysis, reduction or the like.

(i)Hydrolysis

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0] non-5-ene, 1,4-diazabicyclo[2.2.2] octane, 1,8-diazabicyclo[5.4.0] undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, hydrogen chloride, hydrogen bromide, etc.]. The elimination using trihaloacetic acid [e.g. trichloroacetic acid, trifluoroacetic acid, etc.] or hydrogen bromide-acetic acid solution is preferably carried out in the presence of cation trapping agents [e.g. anisole, phenol, etc.].

The reaction is usually carried out in a solvent such as water, alcohol [e.g. methanol, ethanol, etc.], methylene chloride, tetrahydrofuran, a mixture thereof or any other solvent which does not adversely influence the reaction. A liquid base or acid can be also used as the solvent.

The reaction temperature is not critical and the reaction is usually carried out under cooling to heating.

(ii)Reduction

The reduction is carried out in a conventional manner including chemical reduction and catalytic reduction.

Suitable reducing agents to be used in chemical reduction are a combination of a metal [e.g. tin, zinc, iron, etc.] or a metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide or a mixture thereof. Additionally, in case that the above-mentioned acids to be used in chemical reduction are liquid, they can also be used as a solvent. Further, a suitable solvent to be used in catalytic reduction may be the above-mentioned solvent and other conventional solvent such as diethyl ether, dioxane, tetrahydrofuran, etc.,or a mixture thereof.

The reaction temperature of this reaction is not critical and the reaction is usually carried out under cooling to heating.

Subprocess [3]

The compound (I) or a salt thereof can be prepared by reacting the compound (II) or a salt thereof with the compound(III) or its reactive derivative at the carboxy group, the sulfo group or the hydroxy group or a salt thereof.

Suitable reactive derivative at the carboxy group or the sulfo group of the compound (III) can be reffered to the ones as exemplified for the compound (VI).

In case that A of the compound (III) is lower alkylene, suitable reactive derivative at the hydroxy group of the compound (III) may include an acid residue.

This reaction can be carried out in substantially the same manner as Subprocess [1].

Process 2

Subprocess [1]

The compound (II) or a salt thereof can be prepared by reacting the compound (Vb) or a salt thereof with the compound (VI) or its reactive derivative at the carboxy group or the sulfo group or a salt thereof.

Suitable salts of the compound (Vb) can be reffered to the ones as exemplified for the compound (I).

This reaction can be carried out in substantially the same manner as Subprocess [1] of Process 1.

Subprocess [2]

The compound (I) or a salt thereof can be prepared by reacting the compound (II) or a salt thereof with the compound (III) or its reactive derivative at the carboxy group, the sulfo group or the hydroxy group or a salt thereof.

This reaction can be carried out in substantially the same manner as Subprocess [3] of Process 1.

In the preparation manner of the present invention, the compound (II) can be used in the subsequent subprocess without isolation.

The compounds obtained by the above processes can be isolated and purified by a conventional method such as pulverization, recrystallization, column chromatography, reprecipitation, or the like.

The object compound (I) and pharmaceutically acceptable salts thereof possess a strong potentiation of the cholinergic activity and they are useful for treating disorders in the central nervous system, especially for treating amnesia, dementia, senile dementia, and the like in human being.

One object of the present invention is to provide the novel processes for preparing the compound (I) or a salt thereof as described above.

The present invention is based on finding that the processes for preparing the object compound (I) and pharmaceutically acceptable salts thereof by using novel intermediates (II) and (IV) are superior to the known processes in yield, purity, and the like.

The following Preparations and Examples are given for the purpose of illustrating the present invention in more detail.

PREPARATION 1

To a mixture of anhydrous piperazine (185 g) and water (650 ml) was added gradually conc hydrochloric acid (650 ml) below 25° C. To this solution was added dropwise an aqueuos solution of sodium nitrite (148 g) in water (370 ml) under stirring at −10—5° C. for a period of about 15 minutes. The reaction mixture was stirred for 2.5 hours at −10—5° C. and then the insoluble matter was filtered off and washed with water (50 ml) The filtrate and the washing were combined and to the resultant mixture was added gradually an aqueuos solution of sodium hydroxide (312 g) in water (781 ml) under stirring at −5—12° C. for a period of about 30 minutes. To the reaction mixture was added dropwise benzyloxycarbonyl chloride (307 ml) under stirring at −12~5° C. for a period of about 15 minutes and the mixture was stirred for 1.5 hours at 5~8° C. An additional benzyloxycarbonyl chloride. (20 ml) was added dropwise to the mixture under stirring at 7~8° C. for a period of about 3 minutes and the mixture was stirred for 1.5 hours at 5~8° C. The reaction mixture was extracted twice with methylene chloride (11×2) and the combined extract was dried over magnesium sulfate and then evaporated in vacuo to give crude 1-benzyloxycarbonyl-4-nitrosopiperazine (540 g) as a pale yellow oil. The substance was not purified further and was used as a raw material for the next reaction.

NMR(CDCl$_3$, δ): 3.45–3.57 (2H), 3.70–3.88 (4H), 4.21–4.32 (2H), 5.18 (2H, s), 7.37 (5H, s)

PREPARATION 2

To a mixture of crude 1-benzyloxycarbonyl-4-nitrosopiperazine (539 g), acetic acid (615 ml) and water (615 ml) was added gradually zinc powder (422 g) under stirring and cooling in an ice-bath at 8~13° C. for a period of 2 hours.

After the ice-bath was removed, the mixture was stirred for 2 hours and liquid temperature reached to 60° C. The mixture was stirred for 2 hours further while adjusting liquid temperature at 30~35° C. in an ice-bath and then the insoluble matter was filtered off by using cellulose powder CF-11 as a filter aid and washed with methanol(11). The filtrate and the washing were combined and poured gradually into the mixture of methylene chloride (400 ml),sodium hydroxide (440 g) and water (1.21) under stirring and cooling in an ice-bath below 35° C.

The insoluble matter was filtered off by using cellulose powder CF-11 as a filter aid and washed with methylene chloride (21).

The filtrate and the washing were combined and then organic layer was separated and aqueous layer was extracted with methylene chloride (11).

The combined organic layer was washed with water (11), dried over magnesium sulfate and then evaporated in vacuo to give crude 1-amino-4-benzyloxycarbonylpiperazine (433 g) as a pale yellow oil. The substance was not purified further and was used as a raw material for the next reaction.

NMR(CDCl$_3$, δ): 2.58 (4H, t, J=4Hz), 3.57 (4H, t, J=4Hz), 5.12 (2H, s), 7.34 (5H, s)

EXAMPLE 1

Crude 1-amino-4-benzyloxycarbonylpiperazine (433 g) and triethylamine (254 ml) were dissolved in dry methylene chloride(1.81) and to this solution was added dropwise p-fluorobenzoyl chloride (225 g) under cooling in an ice-bath at 8~25° C. for a period of 20 minutes. The reaction mixture was stirred for 1 hour at ambient temperature and then the resultant crystal was collected by filtration and washed with methylene chloride (300 ml), diisopropyl ether (500 ml) and water (1.51) successively to give N-(4-benzyloxycarbonyl-1-piperazinyl)-4-fluorobenzamide (327 g) as a white powder.

NMR(CDCl$_3$, δ): 2.91 (4H, s), 3.70 (4H, s), 5.12 (2H, s), 7.10 (2H, t, J=8Hz), 7.34 (5H, s), 7.75 (2H, dd, J=8, 6Hz)

EXAMPLE 2

To a mixture of 30% hydrogen bromide-acetic acid solution (844 ml) and anisole (53 ml) was added gradually N-(4-benzyloxycarbonyl-1-piperazinyl)-4-fluorobenzamide (327 g) under nitrogen atmosphere with stirring for a period of 15 minutes.

Liquid temperature rose to 40° C. from 25° C. and the reaction mixture turned to a clear solution. The reaction mixture was stirred for 3.5 hours at ambient temperature, the resultant crystal was collected by filtration and washed with diethyl ether (200 ml) to give the first crystal (229 g) of N-(1-piperazinyl)-4-fluorobenzamide hydrobromide as a white powder. Further mother liquor is evaporated in vacuo and the residue was washed with diethyl ether (800 ml) to give the second crystal (162 g) as a pale brown powder. Since both the first crystal and the second crystal are extremely hygroscopic, the crystals were brought in a desicator immediately after filtration and dried at ambient temperature.

Then to a mixture of crude crystal (391 g) of N-(1-piperazinyl)-4-fluorobenzamide hydrobromide obtained by the method described above and 1N aqueous solution of sodium hydroxide (21) was added gradually acetic anhydride (130 ml) under cooling in an ice-bath at 15~20° C. After being stirred for several minutes, whole reaction mixture solidified to enable no stirring. After being stood for 1 hour at 20° C., the crystal was collected by filtration and washed with water (21) and diisopropyl ether (11) successively to give a white powder (228 g). After air drying overnight, the powder was suspended in diisopropyl ether (11) and stirred for 3 hours at ambient temperature. The crystal was collected by filtration and washed with diisopropyl ether to give a white powder (183 g). After the powder was dissolved in 20% aqueous solution of ethanol (1.11) by heating, the hot solution was filtered and the filtrate was stood for 1.5 hours in an ice-bath. Separated crystal was collected by filtration, washed with 20% aqueous solution of ethanol (550 ml) and then air-dried overnight to give N-(4-acetyl-1-piperazinyl)-4-fluorobenzamide (163.3 g) as a white crystalline powder.

mp: 209–210° C.

We claim:

1. A compound of the formula:

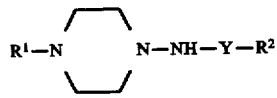

wherein R$^1$ is hydrogen or benzyloxycarbonyl, $R^2$ is cyclo(lower)alkyl, aryl or ar(lower)alkyl, each of which may be substituted with halogen and

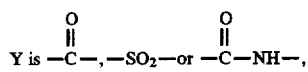

or a pharmaceutically acceptable salt thereof.

2. N-(4-benzyloxycarbonyl-1-piperazinyl)-4-fluorobenzamide.

3. A process for the preparation of a compound of the formula:

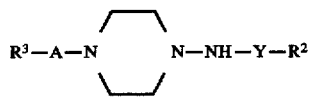

or a pharmaceutically acceptable salt thereof which comprises reacting a compound of the formula:

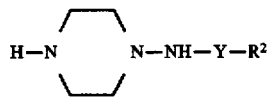

or a pharmaceutically acceptable salt thereof with a compound of the formula:

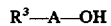

or its reactive derivative or a pharmaceutically acceptable salt thereof, wherein $R^2$ is cyclo(lower)alkyl, aryl or ar(lower)alkyl, each of which may be substituted with halogen, $R^3$ is lower alkyl, aryl, ar(lower)alkoxy or heterocyclic group, each of which may be substituted with halogen,

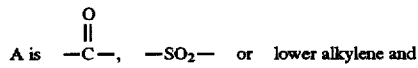

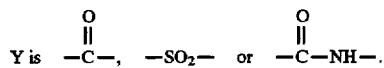

4. A process for the preparation of a compound of the formula:

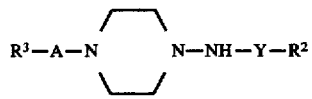

or a pharmaceutically acceptable salt thereof, which comprises i) subjecting a compound of the formula:

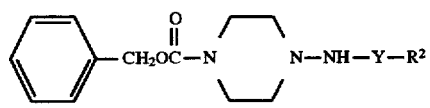

to elimination reaction of the benzyloxycarbonyl group to give a compound of the formula:

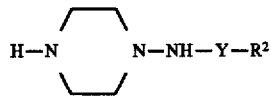

or a pharmaceutically acceptable salt thereof and then ii) reacting the compound obtained or the pharmaceutically acceptable salt thereof with a compound of the formula:

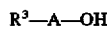

or its reactive derivative or a pharmaceutically acceptable salt thereof, wherein $R^2$ is cyclo(lower)alkyl, aryl or ar(lower)alkyl, each of which may be substituted with halogen, $R^3$ is lower alkyl, aryl, ar(lower)alkoxy or heterocyclic group, each of which may be substituted with halogen, A is

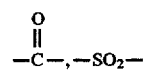

or lower alkylene and

Y is

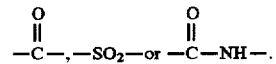

5. The compound as claimed in claim 1 wherein $R^2$ is cyclo(lower)alkyl, or phenyl, each of which may be substituted with halogen.

6. The process as claimed in claim 3 wherein $R^2$ is cyclo(lower)alkyl, or phenyl, each of which may be substituted with halogen and $R^3$ is lower alkyl, phenyl, naphthyl, tolyl, xylyl, mesityl, cumenyl or thienyl.

7. The process as claimed in claim 4 wherein $R^2$ is cyclo(lower)alkyl, or phenyl, each of which may be substituted with halogen and $R^3$ is lower alkyl, phenyl, naphthyl, tolyl, xylyl, mesityl, cumenyl or thienyl.

* * * * *